United States Patent [19]

Merger et al.

[11] Patent Number: 5,380,919
[45] Date of Patent: Jan. 10, 1995

[54] PREPARATION OF NEOPENTYL GLYCOL HYDROXYPIVALATE

[75] Inventors: Franz Merger, Frankenthal; Martin Schmidt-Radde, Ludwigshafen, both of Germany

[73] Assignee: BASF Aktiengesellschaft, Ludwigshafen, Germany

[21] Appl. No.: 32,025

[22] Filed: Mar. 16, 1993

[30] Foreign Application Priority Data

Mar. 18, 1992 [DE] Germany ............... 4208571

[51] Int. Cl.⁶ ................................. C07C 69/675
[52] U.S. Cl. ................................... 560/179
[58] Field of Search .......................... 560/179

[56] References Cited

U.S. PATENT DOCUMENTS

| | | |
|---|---|---|
| 3,641,117 | 2/1972 | Platz et al. |
| 3,852,335 | 12/1974 | Merger et al. ............... 260/484 R |
| 3,862,215 | 1/1975 | Merger et al. |
| 4,273,934 | 6/1981 | Merger et al. ............... 560/238 |
| 5,024,772 | 6/1991 | Thurman et al. ............... 252/1 |
| 5,041,621 | 8/1991 | Morris et al. ............... 560/189 |
| 5,185,478 | 2/1993 | Salek et al. ............... 568/853 |
| 5,209,827 | 5/1993 | Butler et al. ............... 203/72 |

FOREIGN PATENT DOCUMENTS 1643650 10/1972 Germany.
2234110 12/1976 Germany.

OTHER PUBLICATIONS

Fouquet et al., Liebigs Ann. Chem. (1979) 1591–1601.

*Primary Examiner*—José G. Dees
*Assistant Examiner*—Barbara S. Frazier
*Attorney, Agent, or Firm*—Keil & Weinkauf

[57] ABSTRACT

A process for preparing neopentyl glycol hydroxypivalate by base-catalyzed disproportionation of hydroxypivalaldehyde, wherein the reaction is carried out in the presence of a readily water-soluble alkaline earth metal salt and of an alkali metal hydroxide.

9 Claims, No Drawings

PREPARATION OF NEOPENTYL GLYCOL HYDROXYPIVALATE

The present invention relates to an improved process for preparing neopentyl glycol hydroxypivalate by base-catalyzed disproportionation of hydroxypivalaldehyde.

Alkaline earth metal hydroxides are disclosed in DE-A 16 43 650 as catalysts for the reaction of hydroxypivalaldehyde to give neopentyl glycol hydroxypivalate. Alkaline earth metal oxides are also suitable for this purpose according to DE-A 22 34 110.

In the industrial embodiment, the disadvantage of thee catalysts is that they must be metered as solids. This requires, especially on continuous operation, a considerable technical expense.

With sodium or potassium hydroxide as catalyst the reaction is non-specific; the Cannizzaro reaction occurs as unwanted side reaction (Liebigs Ann. Chem. (1979) 1591–1601).

It is an object of the present invention to provide a process which does not involve metering the catalyst as solid.

We have found that this object is achieved by a process for preparing neopentyl glycol hydroxypivalate by base-catalyzed disproportionation of hydroxypivalaldehyde, wherein the reaction is carried out in the presence of a readily water-soluble alkaline earth metal salt and of an alkali metal hydroxide.

The reaction can be illustrated by the following equation:

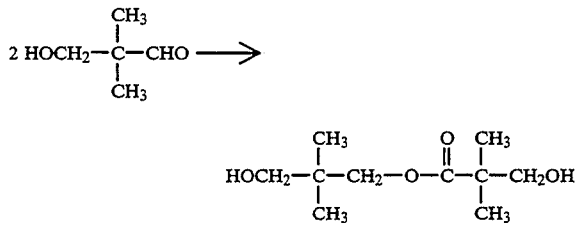

The hydroxypivalaldehyde used as starting material can be prepared, for example, from isobutyraldehyde and aqueous formaldehyde with trialkylamine catalysis (EP-A 0 173 976). Both the crude product from this reaction and the purified product are suitable as starting materials. Hydroxypivalaldehyde is normally employed with a water content of from 1 to 50% by weight, preferably from 4 to 20% by weight.

Suitable alkaline earth metal salts are readily water-soluble salts such as halides or carboxylates and the hydrates thereof. Readily water-soluble means that the solubility at 25° C. is at least 10 g/l of water. Salts of calcium, strontium and barium are preferred, especially the calcium salts. Examples are: calcium chloride, calcium bromide, calcium iodide, calcium formate, calcium acetate, calcium propionate, calcium butyrate, calcium isobutyrate, calcium α-methylbutyrate, barium chloride, barium bromide, barium iodide, barium formate, barium acetate, barium propionate, strontium chloride, strontium bromide, strontium iodide, strontium formate, strontium acetate and strontium lactate.

The alkaline earth metal salts can be employed in an amount of from 0.5 to 15, preferably 0.5 to 8, mol % based on hydroxypivalaldehyde.

They are preferably added in the form of aqueous solutions, particularly preferably in the form of concentrated aqueous solutions, to the reaction mixture.

Suitable alkali metal hydroxides are the hydroxides of lithium, sodium and potassium, and sodium hydroxide is preferred. In general, from 1 to 3 mol of alkali metal hydroxide, preferably from 1.8 to 2.5 mol per mol of alkaline earth metal salt. The alkali metal hydroxides are likewise preferably employed as concentrated aqueous solutions, but can also be used as dilute solutions.

One possible embodiment of the invention is to add the alkali metal hydroxide to a solution which contains hydroxypivalaldehyde and a readily water-soluble calcium salt. In the converse case, i.e. on addition of a readily water-soluble calcium salt to a solution which contains hydroxypivalaldehyde and an alkali metal hydroxide, there may be formation of unwanted by-products. It has proven particularly advantageous, especially for continuous processes, to add separate solutions of the two catalyst components to the hydroxypivalaldehyde.

The reaction is carried out batchwise or continuously, preferably continuously. Suitable in the latter case are conventional reactors such as tubular reactors, cascades of stirred vessels and multichamber bubble columns. Particularly good results are obtained with multichamber bubble columns.

The reaction is preferably carried out at from 40° to 100° C., particularly at from 60° to 80° C. Since the pressure has no detectable effect on the process, it is preferably carried out under atmospheric pressure.

Under the stated conditions, the reaction time for virtually complete conversion in the continuous procedure is about 2–60, usually 5–25, minutes.

The weakly basic discharge from the reactor can then be worked up to give the product by conventional methods (e.g. EP-A 0 173 976) or used directly for further reactions. Thus, the weakly basic discharge from the reactor is preferably mixed with from 0.5 to 2 mol of an acid (based on 1 mol of basic catalyst component) so that the reaction mixture is slightly acid or, preferably, neutral, and is extracted with water at from 50° to 100° C.

The neopentyl glycol hydroxypivalate is isolated by distillation by conventional methods.

The process according to the invention makes it possible to prepare neopentyl glycol hydroxypivalate from hydroxypivalaldehyde in high yield with the technical advantage that only metering of solutions is necessary.

Neopentyl glycol hydroxypivalate is a valuable starting material for preparing polyesters, synthetic resins and plasticizers.

EXAMPLES

Example 1

A liquid phase process was carried out in a multichamber bubble column reactor (volume=251 ml; length=80 cm; diameter=2 cm; 9 perforated plates 8 cm apart; 3 perforations with a diameter of 3 mm in each plate) which was maintained at 70° C. by an oil-filled jacket by passing per hour 800 ml of hydroxypivalaldehyde (HPA) with a water content of 5% (7.3 mol of HPA), 171 ml of a 22% by weight aqueous calcium acetate solution (3.3 mol % calcium acetate based on HPA) and 36 ml of a 40% by weight aqueous NaOH solution (6.6 mol % NaOH based on HPA). This corresponds to a holdup time of 15 min and a total water content of the reaction mixture of 21.2%. Efficient mixing of the contents of the bubble column was achieved by additionally passing in 17 l/h nitrogen. The discharge from the reactor was neutralized with 2.1 g of concentrated formic acid per 100 g of discharge, after which the phases were separated at 70° C., and the product was isolated by distillation.

The yield of neopentyl glycol hydroxypivalate was 91%.

Example 2

A liquid phase process was carried out in a multi-chamber bubble column reactor as in Example b 'by passing at 70° C. per hour 928 ml of hydroxypivalaldehyde with a water content of 17% (6.9 mol of HPA), 45.9 ml of a 34% by weight aqueous $CaCl_2$ solution (2.7 mol % $CaCl_2$ based on HPA) and 31.2 ml of a 40% by weight aqueous NaOH solution (5.8 mol % NaOH based on HPA). This corresponds to a holdup time of 15 min and a total water content of the reaction mixture of 22%. Efficient mixing of the contents of the bubble column was achieved by additionally passing through 17 l/h nitrogen. The discharge from the reactor was neutralized with 2.0 g of concentrated formic acid per 100 g of discharge, after which the phases were separated at 70° C., and the product was isolated by distillation.

The yield of neopentyl glycol hydroxypivalate was 92%.

We claim:

1. A process for preparing neopentyl glycol hydroxypivalate by base-catalyzed disproportionation of hydroxypivalaldehyde, which comprises: carrying out in the presence of an aqueous solution of a readily water-soluble alkaline earth metal salt and of an alkali metal hydroxide.

2. The process of claim 1, wherein the alkali metal hydroxide is sodium or potassium hydroxide.

3. The process of claim 2, wherein the alkaline earth metal salt is a calcium, strontium or barium halide or carboxylate or a hydrate thereof.

4. The process of claim 2, wherein the alkaline earth metal salt is a calcium chloride, calcium bromide, calcium iodide, calcium formate, calcium acetate or calcium propionate.

5. A continuous process for preparing neopentyl glycol hydroxypivalate by the base-catalyzed disproportionation of hydroxypivalaldehyde which comprises: continuously adding an aqueous solution of a readily water-soluble alkaline earth metal salt and a separate aqueous solution of an alkali metal hydroxide to the hydroxypivalaldehyde.

6. The process of claim 5, wherein sodium or potassium hydroxide is used as the alkali earth metal hydroxide.

7. The process of claim 6, wherein the alkaline earth metal salt is a calcium, strontium or barium halide or carboxylate or a hydrate thereof.

8. The process of claim 6, wherein the alkaline earth metal salt is a calcium chloride, calcium bromide, calcium iodide, calcium formate, calcium acetate or calcium propionate.

9. The process of claim 5, wherein the disproportionation mixture is neutralized and then distilled to isolate the neopentyl glycol hydroxypivalate.

* * * * *